United States Patent [19]
Reinkensmeyer

[11] Patent Number: 5,830,160
[45] Date of Patent: Nov. 3, 1998

[54] MOVEMENT GUIDING SYSTEM FOR QUANTIFYING DIAGNOSING AND TREATING IMPAIRED MOVEMENT PERFORMANCE

[76] Inventor: David J. Reinkensmeyer, 2609 W. Fitch Ave., Chicago, Ill. 60611

[21] Appl. No.: 844,143

[22] Filed: Apr. 18, 1997

[51] Int. Cl.$^6$ .................................................. A61B 5/00
[52] U.S. Cl. ............................................................ 600/595
[58] Field of Search .................................. 600/587, 595; 73/379.01–379.03

[56] References Cited

U.S. PATENT DOCUMENTS

| | | | |
|---|---|---|---|
| 4,235,437 | 11/1980 | Ruis et al. | 272/134 |
| 4,550,908 | 11/1985 | Dixon | 272/130 |
| 4,607,841 | 8/1986 | Gala | 272/125 |
| 4,620,703 | 11/1986 | Greenhut | 272/129 |
| 4,665,928 | 5/1987 | Linial et al. | 128/782 |
| 4,702,108 | 10/1987 | Amundsen et al. | 73/379 |
| 4,711,450 | 12/1987 | McArthur | 272/129 |
| 4,889,108 | 12/1989 | Bond et al. | 128/25 R |
| 4,907,797 | 3/1990 | Gezari et al. | 272/129 |
| 4,919,418 | 4/1990 | Miller | 272/129 |
| 4,921,244 | 5/1990 | Berroth | 272/117 |
| 4,934,694 | 6/1990 | McIntosh | 272/129 |
| 4,974,830 | 12/1990 | Genovese et al. | 272/25 R |
| 5,050,618 | 9/1991 | Larsen | 128/774 |
| 5,054,774 | 10/1991 | Belsito | 272/130 |
| 5,078,152 | 1/1992 | Bond et al. | 128/774 |
| 5,179,939 | 1/1993 | Donovan et al. | 128/25 R |
| 5,201,772 | 4/1993 | Maxwell | 623/24 |
| 5,209,715 | 5/1993 | Walker et al. | 482/137 |
| 5,215,510 | 6/1993 | Baran | 482/104 |
| 5,263,492 | 11/1993 | Voyce | 128/782 |
| 5,277,681 | 1/1994 | Holt | 482/112 |
| 5,314,390 | 5/1994 | Westing et al. | 482/6 |
| 5,331,851 | 7/1994 | Parviainen et al. | 73/379.01 |
| 5,373,858 | 12/1994 | Rose et al. | 128/782 |
| 5,375,610 | 12/1994 | LaCourse et al. | 128/782 |
| 5,417,643 | 5/1995 | Taylor | 601/33 |
| 5,421,798 | 6/1995 | Bond et al. | 601/23 |
| 5,435,321 | 7/1995 | McMillen et al. | 128/782 |
| 5,454,773 | 10/1995 | Blanchard et al. | 482/133 |
| 5,466,213 | 11/1995 | Hogan et al. | 601/33 |
| 5,484,389 | 1/1996 | Stark et al. | 601/34 |
| 5,509,878 | 4/1996 | Denega et al. | 482/110 |
| 5,524,645 | 6/1996 | Wills | 128/898 |

OTHER PUBLICATIONS

"Multi–Joint System 2AP," Copyright 1993, Biodex Medical Systems, Inc. 1993; Biodex, Shirley, NY.

"Quantification of Weakness & Muscle Synergies in Hemiparetic Stroke Subjects: Preliminary Results;" Beer, Dewald, Given & Schultz; Rehab Inst. of Chgo.; Presented at Society of Neuroscience, 1995.

"Stability Properties of Human Reaching Movements;" Hogan; Massachusetts Institutes of Technology, Cambridge, Massachusetts; Experimental Brain Research 107(1):125–36, 1995.

"Quantitative Assessment of Four Men Using Above–Elbow Prosthetic Control;" Popat, Krebs, Mansfield, etc.; Archives of Phys. Medicine & Rehab 74(7):720–9, 1993 Jul.; Mass. Gen. Hosp. Inst. Boston, MA.

"Visual Control of Arm Movement in the Stroke Patient;" Lough; Intl. Journal of Rehab Research, Supp No. 5, vol. 10, No. 4 (1987); Rehab . International, Published by HVA Edit. Schindele; pp. 113–119.

"Cybex and You . . . Partners in Success;" Cybex; Ronkonkoma, LI, New York; Copyright 1994, Cybex, 2A010 May 1994.

(List continued on next page.)

*Primary Examiner*—Max Hindenburg
*Attorney, Agent, or Firm*—Gardner, Carton & Douglas

[57] ABSTRACT

The present invention provides a guide that can be used to quantify impaired movement performance of a limb, to diagnose whether passive, active, or reflexive impairments limit movement performance, to quantify the resistance to movement provided by the limb at the workspace boundary, and to provide a means for a user to practice improving movement performance of the limb.

41 Claims, 12 Drawing Sheets

OTHER PUBLICATIONS

"Cybex and You . . . a Total Partnership;" Cybex; Ronkonkoma, LI, New York; Copyright 1995, Cybex 2A010 6.95.

"BTE Dynatrac;" Copyright 1992, Baltimore Therapeutic Equipment Co.; Hanover, Maryland; Form No. 501–92.

"The Lido Active MJ;" Loredan Biomedical, Inc.; West Sacramento, California; Copyright 1994 Loredan Biomedical, Inc.; 940056–01 Rev A.

"The Lido Linea;" Loredan Biomedical, Inc.; West Sacramento, California; Copyright 1994 Loredan Biomedical, Inc.; 940079–01 Rev A.

"Kin–Com;" Wellness by Design; Chattanooga Group, Inc., Hixson, Tennessee; Copyright 1995 Chattanooga Group, Inc.; Form 10045.

"MIT–Manus: A Workstation for Manual Therapy and Training I;" Hogan, Krebs, Charnnarong, Srikrishna and Sharon; Newman Lab. for Biomechanics & Human Rehab.; MIT–3–137; Cambridge, MA; Jun. 1992.

MOVEMENT GUIDING SYSTEM FOR QUANTIFYING DIAGNOSING AND TREATING IMPAIRED MOVEMENT PERFORMANCE

This invention was made with U.S. Government support under Grant Number 1F32HD08067-01 awarded by the National Institutes of Health. The government has certain rights in the invention.

FIELD OF THE INVENTION

This invention relates in general to quantification, diagnosis, and treatment of impaired movement performance and, in particular, to a method and apparatus for quantifying, diagnosing, and treating impaired movement performance of the arms or legs.

BACKGROUND OF THE INVENTION

When a person suffers brain injury from stroke, trauma or another cause, the person's ability to control movement of the arms and legs often decreases. The most common limiting factor is hemiplegia, or weakness on one side of the body. This weakness is due primarily to destruction of neural outflow pathways from the brain to the muscles.

Besides hemiplegia, several other impairments can significantly limit movement performance. Involuntary tonic muscle activity, changed connective tissue stiffness, and hyperactive muscle stretch reflexes may restrict movement. In addition, movement often appears to be limited by relatively tight, stereotypical coupling of motion at adjacent joints. Such stereotypical coupling of motion is clinically referred to as an "abnormal synergy." Abnormal synergies are attributed to uncontrolled, simultaneous activation of muscles acting at adjacent joints.

A common consequence of these motor impairments is a decrease in the capacity of the affected limb to generate force in arbitrary directions. As a result, the limb may have difficulty moving in some directions. In addition, the limb's workspace may be decreased.

Many devices are available for quantifying the force generating capability of a limb during movement. One common approach is to mechanically guide the limb along a specified path and measure the movement and the force generation of the limb tangent to the path. The specified path is typically a line or a circular arc. Resistance or assistance to movement along the specified path is often provided by an actuator or brake. Examples of devices that adopt this approach include U.S. Pat. No. 4,691,694 to Boyd et al.; U.S. Pat. No. 4,711,450 to McArthur; U.S. Pat. No. 4,919,418 to Miller; and U.S. Pat. No. 5,209,715 to Walker et al.

One disadvantage of this approach is that it only measures the force generation tangent to the specified guided movement path. After brain injury, an impaired arm may generate significant forces and torques perpendicular to the guided movement path against the constraint of the guiding device. These perpendicular forces and torques are referred to as "constraint forces." Different patterns of constraint forces may arise depending on the relative predominance of inappropriate tonic muscle activity, changed connective tissue stiffness, hyperactive muscle stretch reflexes, and abnormal synergies. Thus, constraint force patterns measured during guided movement contain valuable information about the causes and severity of impaired movement performance.

Several devices are known that are capable of guiding the movement of a limb along a desired path and measuring constraint forces generated by the limb against the device. However, none of these devices use constraint force patterns to quantify, diagnose, or treat impaired movement performance after brain injury. For example, U.S. Pat. No. 4,235,437 to Ruis et al. is directed toward an automatically controlled exercise machine with a powered linkage. The linkage interacts with the user by means of various removable attachments located on the outermost link. The user interaction point can be made to move along any specified path in response to forces exerted by the user. A force transducer measures two components of force generated by the limb against the linkage in the plane of movement. These components are used to compute the tangent force to the direction of movement. However, the perpendicular component of force to the direction of movement is not used to quantify, diagnose, or treat impaired movement performance.

U.S. Pat. No. 5,466,213 to Hogan et al. is directed toward an interactive robotic therapist that guides a patient's limb along a desired path through a desired series of exercises. The robotic therapist incorporates sensors that provide position, velocity, and force information at the patient's hand. The reference, however, does not teach using constraint force information to quantify, diagnose, or treat impaired movement performance.

U.S. Pat. No. 5,421,798 to Bond et al. is directed toward an apparatus for evaluation of a limb of a test subject. The distal end of the limb is secured to the apparatus. The test subject moves the limb along a linear track. At least two components of the forces generated by the limb against the track are sensed. The force components are used to calculate the forces applied at each limb joint contributing to movement. The reference, however, does not teach using constraint force information to quantify, diagnose, or treat impaired movement performance.

Thus, it is an object of the present invention to provide a means for quantifying movement performance of an impaired limb.

It is another object of the present invention to provide a means for diagnosing the relative contributions of different motor impairments to the movement performance of an impaired limb.

It is yet another object of the present invention to provide a means for the user to practice improving movement performance of an impaired limb.

It is a further object of this invention to provide a means for identifying regions of an impaired limb's workspace into which the limb has difficulty moving.

It is another object of this invention to provide a means for diagnosing the relative contributions of different motor impairments to workspace deficits.

It is yet another object of this invention to provide a means for the user to practice improving the ability to move the impaired limb into difficult workspace regions.

These and further objects and advantages of the present invention will be apparent from a consideration of the drawings and the ensuing description.

SUMMARY OF THE INVENTION

The present invention provides a guide for guiding movement of the limb along a linear path. The guide can be oriented in different directions and placed in different positions relative to the user. Position sensors measure the position of the limb along the guide. A force sensor measures all the contact forces generated against the guide. A control system records, stores, and displays limb position and constraint forces.

The present invention can be used to quantify movement performance by measuring constraint forces generated during guided movement attempts along a desired path.

The present invention can be used to diagnose underlying impairments to movement performance by comparing the patterns of constraint forces generated during passive and active movements along a desired path. For passive movements, the user attempts to relax, and an outside force, such as another person or an actuator, moves the limb along the guide. For active movements, the user attempts to move the limb along the guide.

Further, the present invention can assist the user in attempts to improve movement coordination by providing feedback about the size and direction of the constraint forces generated during movement attempts along a desired path. Using the feedback, the user can then attempt to match a desired pattern of constraint force. The user's success at matching can be quantified and monitored by the control system.

Similarly, the present invention can be used to identify regions of the limb's workspace into which the user has difficulty moving the limb. This is accomplished by orienting the guide so that movement is directed into the workspace region to be tested and then measuring the extrema of movement achievable by the user along the guide.

Additionally, the present invention can be used to diagnose the cause of workspace deficits by comparing the extent of movement achieved during passive and active guided movements of the limb. It also can be used to diagnose the degree of impaired force generation at the workspace boundary by measuring the constraint force generated by the limb at the workspace boundary. It further can be used to quantify the resistance to movement of an impaired limb at the boundary of the limb's workspace.

The present invention can help the user in attempting to improve movement performance by guiding movement attempts into difficult workspace regions. During guided movement attempts, motivating feedback is provided to the subject about the extent of movement into difficult workspace regions.

Millions of people in the U.S. currently suffer from motor impairment due to brain injury. Much of their diagnosis, monitoring, and treatment is done subjectively by manual and visual observations of the impaired limb. The present invention can improve diagnosis by helping a doctor or therapist to better quantify the causes of impaired movement. More accurate diagnosis can assist in more effectively targeting therapy, thereby improving recovery of the patient.

The present invention can improve patient monitoring by helping objectively track the patient's progress and the effects of treatment in improving motor ability. The device can be used by clinicians, patients, and insurance companies as a means to justify on-going treatment, and as a basis for decisions on terminating, redirecting, or continuing therapy. The present invention can also help to sensitively and objectively distinguish the effects of various drug and therapeutic interventions.

The present invention can also be used as a treatment tool. It can provide a means for implementing motor exercises targeted at specific movements with which a patient has difficulty. It can provide physical guidance and detailed feedback to patients during exercise to help improve performance of those movements. Patients could use the devices in a clinic, thereby helping to reduce the one-on-one interaction time needed with therapists and the overall cost of treatment. Portable versions designed for home use could also be provided, enabling victims of brain injury to continue therapy and improve motor performance on their own.

DESCRIPTION OF THE PREFERRED EMBODIMENT

Figure 1:
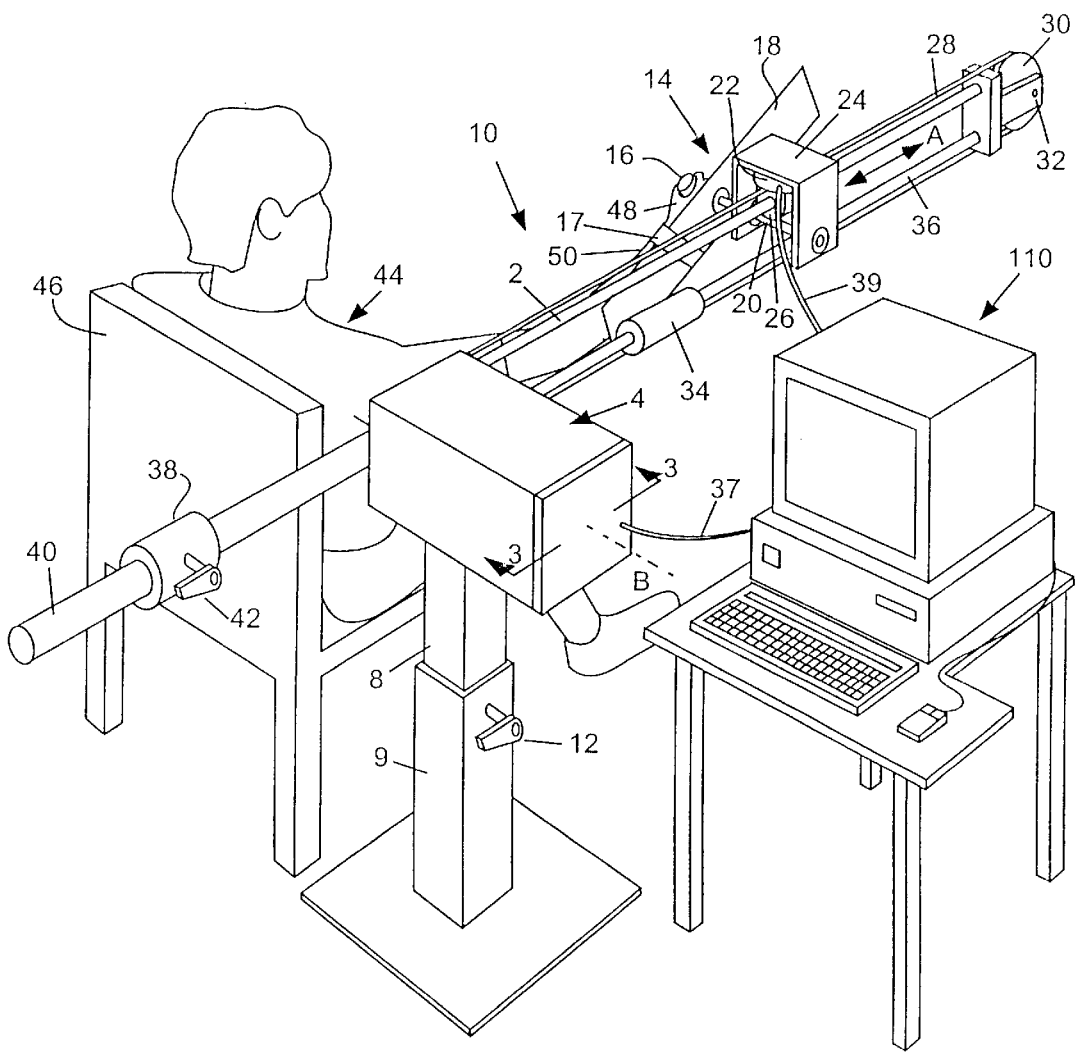
FIG. 1 is a perspective view of a user interacting with the preferred embodiment of the guide of the present invention.

Referring first to FIG. 1, a guide 10 made in accordance with the principles of the present invention is seen. The guide 10 includes a splined shaft 2 operatively coupled to a drive box 4. Drive box 4 communicates with a control system 110 via cable 37. Drive box 4 is supported by a support column 8. The height of the drive box can be adjusted by loosening a clamp 12 and sliding the column with respect to a base 9 of the support. The column and thus the drive box can be locked at the desired height by tightening clamp 12. This arrangement allows the drive box 4 to be vertically adjusted and to be used with a number of different sized users.

The guide 10 further includes a user-attachment interface 14. The user-attachment interface further includes a cone handle 16, a forearm brace 18, a forearm strap 17, a rotary shaft 20, and a shaft holder 24. In an alternate embodiment, the user attachment interface could take a different form, for example, a splint molded to the shape of the hand. In the preferred embodiment of the present invention, a user 44 grasps the cone handle 16 with one hand 48. The user's forearm 50 is strapped into the forearm brace 18 using the forearm strap 17. The cone handle 16 is attached to the forearm brace 18 which is operatively connected to the rotary shaft 20. Rotary shaft 20 in turn is operatively connected to the force sensor 22 via shaft holder 24. Shaft holder 24 is designed to provide low resistance to the rotation of rotary shaft 20.

Force sensor 22 carries a spline nut 26. The spline nut 26 is capable of sliding movement along the splined shaft 2 in the direction of arrow A, thereby carrying user-attachment interface 14 along a linear path. The user-attachment interface 14 is further capable of rotating in such a manner that the user's forearm 50 is allowed to rotate in a plane parallel to the plane of the splined shaft 2 during translation of user-attachment interface 14 along splined shaft 2.

In the preferred embodiment of the present invention, the force sensor 22 measures three orthogonal components of force and three orthogonal components of torque. The force sensor 22 is connected to the control system 110, via cable 39, that records and stores measured force values. The force values are then used to quantify, diagnose and treat impaired movement. For example, the force sensor 22 measures the tangent force generated by the user's hand which in turn is used to determine the resistance to movement at the workspace boundary and the safe threshold in passively stretching the arm. The force sensor 22 is commercially available from Assurance Technologies Incorporated.

Figure 2:
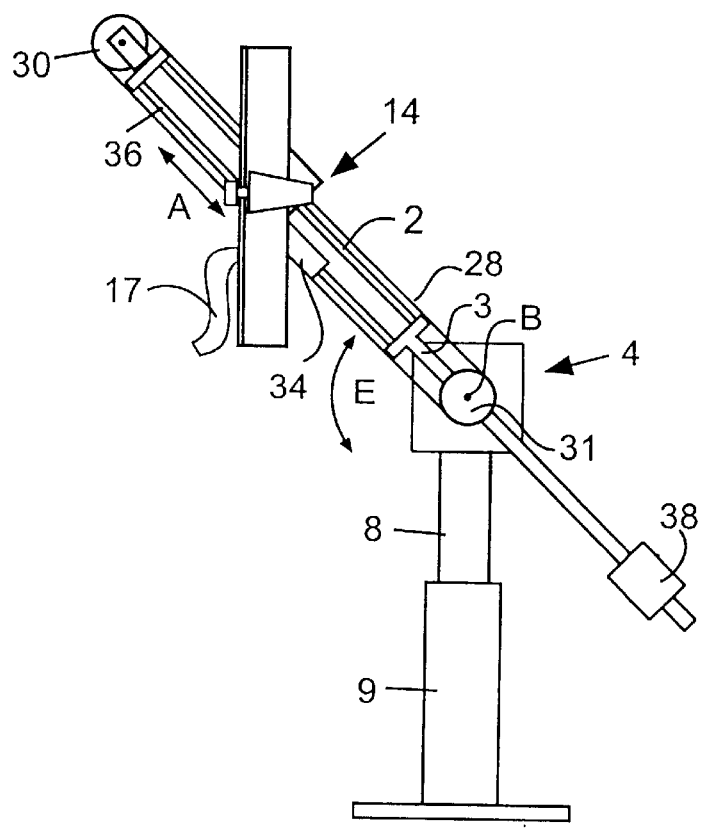
FIG. 2 is a schematic side view of the guide.

The guide is further provided with a cable chain 28 and a sprocket 30. The cable chain 28 is operatively connected to the spline nut 26 beneath force sensor 22. The sprocket 30 is mounted on a rotary shaft 32 at the distal end of splined shaft 2. As seen in FIGS. 1 and 2, the cable chain 28 is operatively coupled to the drive box 4, extends from the drive box 4 adjacent the splined shaft 2, loops around sprocket 30, and then extends back toward the drive box 4.

The guide 10 further includes a counterbalance 34 which is attached to cable chain 28. The counterbalance 34 slides along a second splined shaft 36 in the direction of arrow A. In the preferred embodiment of the present invention, the weight of counterbalance 34 is equal to the combined weight of the spline nut 26, the force sensor 22, and the user-attachment interface 14. Counterbalance 34 translates in the opposite direction and by an equal amount to any movement of the user-attachment interface 14. This is attributed to the counterbalance being attached to the cable chain 28 of distal sprocket 30 on the side opposite the side to which the user-attachment interface 14 is attached. As a result, the center of mass of the forward portion of the guide 10 remains constant as the user attachment interface 14 moves along spline shaft 36. Thus, the torque generated by the forward portion of movement guide 10 about an axis B of drive box 4 remains constant during movement of the user-attachment interface 14.

A rear member 40 extends from the spline shaft 2 in the rear of guide 10. Attached to the rear member 40 is a second counterbalance 38. The counterbalance 38 cancels the constant torque generated by the forward portion of the movement guide 10 about axis B of the drive box 4. The position of counterbalance 38 can be adjusted along the rear member 40 via a clamp 42. Clamp 42 can be tightened to hold counterbalance 38 at a desired position along rear member 40, or loosened to allow counterbalance 38 to be slid to different positions. This adjustment allows for the precise cancellation of the constant torque produced by the forward portion of guide 10 about axis B of the drive box 4. In a further alternate embodiment, weights could be added to counterbalances 34 and 38 to assist or resist the arm as it moves along the constraint.

FIG. 2 illustrates a schematic side view of the guide viewed from the side that a user would be attached to the guide. As can be seen from FIG. 2, cable chain 28 further loops around a second sprocket 31 which is located adjacent the drive box 4. Sprocket 31 is capable of rotating about axis B. Thus, the translation of the user-attachment interface 14 in the direction of arrow A is coupled to the rotation of sprocket 31 about axis B.

Splined shafts 2 and 36 are both coupled to member 3. Member 3 is capable of rotating about axis B, thereby causing the forward portion of the guide to rotate in the direction indicated by an arrow E. The angle of rotation about axis B in the direction of arrow E is referred to as the elevation angle.

As a result of counterbalances 34 and 38, guide 10 remains at any elevation angle in which it is placed. In addition, user 44 experiences no static loading of the arm due to the weight of guide 10 regardless of the elevation angle of the user's arm or the linear position of the user's arm along splined shaft 2.

As can be understood from FIG. 2, guide 10 can be used with either the user's left or right arm. This is accomplished by reversing the direction the user 44 is facing, rotating user-attachment interface 18 which is symmetric about the longitudinal axis of the cone handle 16, and swinging the forward portion of the guide to the opposite side of the column 8.

Figure 3:
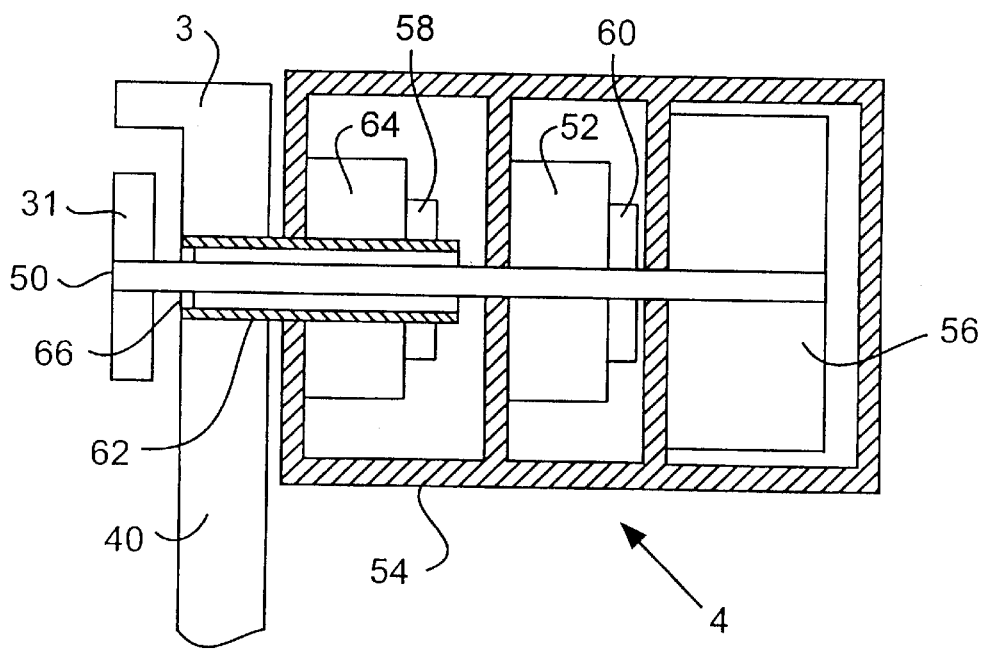
FIG. 3 is a cross-sectional top view of the drive box of the guide of the present invention.

FIG. 3 shows a cross-sectional top view of the drive box 4. Drive box 4 includes a frame 54 in which are housed first braking means 64, second braking means 52 and a motor 56. In the preferred embodiment of the present invention, the braking means comprise magnetic particle brakes. However, it should be understood that alternate equivalent braking means could be used in place of the magnetic particle brakes.

Magnetic particle brake 64 is referred to as the elevation brake and magnetic particle brake 52 is referred to as the reach brake. Elevation brake 64 is associated with a hollow shaft 62 and a position sensor 58 which measures the rotation of hollow shaft 62. Reach brake 52 is associated with a position sensor 60 which measures the rotation of a drive shaft 50. In the preferred embodiment of the present invention, the position sensors comprise optical encoders. However, it should be understood that alternate equivalent position sensing means could be used in place of optical encoders. Further, motor 56 is preferably a direct current torque motor. Alternate equivalent motors, however, can be used for the direct current torque motor.

As shown in FIG. 3, sprocket 31 is operatively coupled to drive shaft 50. Drive shaft 50 extends through a bearing 66 inserted in one end of the hollow shaft 62, through the hollow shaft 62 and the elevation brake 64. The drive shaft 50 continues to extend through the other end of hollow shaft 62 and is operatively connected to reach brake 52 and motor 56. Reach brake 52 can apply braking torque to drive shaft 50 while motor 56 can apply torque to drive shaft 50. Drive shaft 50 is operatively coupled to optical encoder 60 so that optical encoder 60 measures the rotation of drive shaft 50. The rotation of drive shaft 50 is coupled to the rotation of sprocket 31, which in turn is operatively connected to the user-attachment interface 14 via cable chain 28. Thus, the optical encoder 60 measures the linear translation of the user-attachment interface 14 along splined shaft 2. In addition, reach brake 52 and motor 56 can apply forces to the user-attachment interface 14 via cable chain 28.

Member 3 is operatively connected to the one end of the hollow shaft 62. Hollow shaft 62 in turn is operatively coupled to the elevation brake 64 and the optical encoder 58. Because member 3 is also operatively connected to splined shaft 2, elevation brake 64 can hold splined shaft 2 at different elevation angles. Optical encoder 58 measures the elevation angle of the member 3 and the splined shaft 2.

The benefit of extending drive shaft 50 through hollow shaft 62 is that it allows reach brake 52 and motor 56 to be placed on the same side of splined shaft 2 as the elevation brake 64. This allows the user's arm to be placed close to splined shaft 2 during movement attempts, thereby minimizing the bending moment on spline nut 26.

Figure 4:
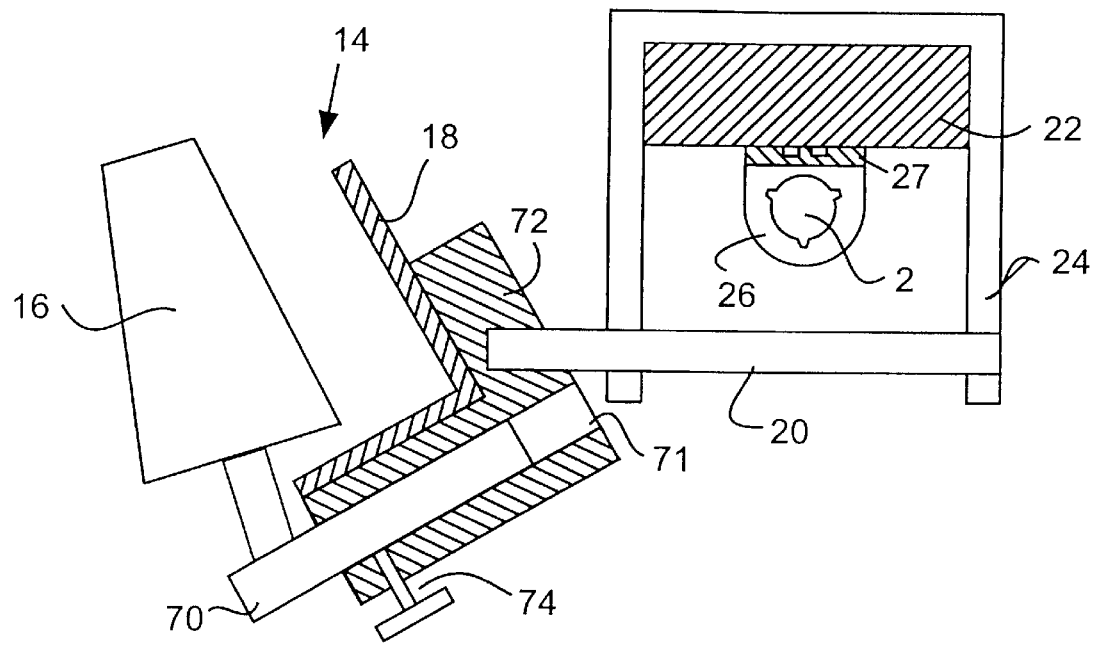
FIG. 4 is a cross-sectional rear view of the user-attachment interface of the guide of the present invention.

Referring to FIG. 4, the user-attachment interface 14 includes the cone handle 16 which is attached to a member 70. Member 70 is capable of sliding through a square hole 71 in a member 72. Forearm brace 18 is also attached to member 72. The forearm brace 18 is preferably tilted to provide a more comfortable position for brain injured users who have trouble fully supinating their forearm. In the preferred embodiment, screws are used to attach the brace 18 to member 72. However, any suitable attaching means could be employed. Due to this arrangement, the cone handle 16 can be slid toward or away from the forearm brace 18 in order to facilitate different users. Member 70 can be locked in a specific position with respect to member 72 by using a clamp 74 screwed into a threaded hole in member 72.

Member 72 is operatively connected to rotary shaft 20 by suitable means such as a clamp. Rotary shaft 20 in turn is attached to shaft holder 24. As stated above, shaft holder 24 provides low resistance to the rotation of rotary shaft 20 so that the cone handle 16 and the forearm brace 18 can freely rotate in a plane parallel to the plane defined by splined shafts 2 and 36. Shaft holder 24 is operatively connected to force sensor 22. Force sensor 22 is attached to a rack 27. The chain 28 is connected to the rack 27 which is in turn bolted to the spline nut 26. Spline nut 26 can translate along splined shaft 2, carrying user interface 14 with it.

To attach a user to the user-attachment interface 14, the clamp 74 is loosened and the cone handle 16 is slid away from the forearm brace 18. As can be seen in FIG. 1, the user's hand 48 is wrapped around the cone handle 16. The user's forearm 50 is then strapped to the forearm brace 18 with strap 17. Cone handle 16 can be slid in against the palm of user's hand 48 to hold user's hand 48 securely between the cone handle 16 and the forearm brace 18. Even if the fingers cannot exert a large enough grasp force to hold onto the cone handle 16, the hand is kept from slipping away from the user-attachment interface 14 by cone handle 16, forearm brace 18, and strap 17. Thus, even if the user 44 has lost the ability to control hand grasp, as is often the case with brain-injured patients, the user's hand 48 and forearm 50 can be held securely in a comfortable position while being firmly attached to guide 10.

Figure 5:
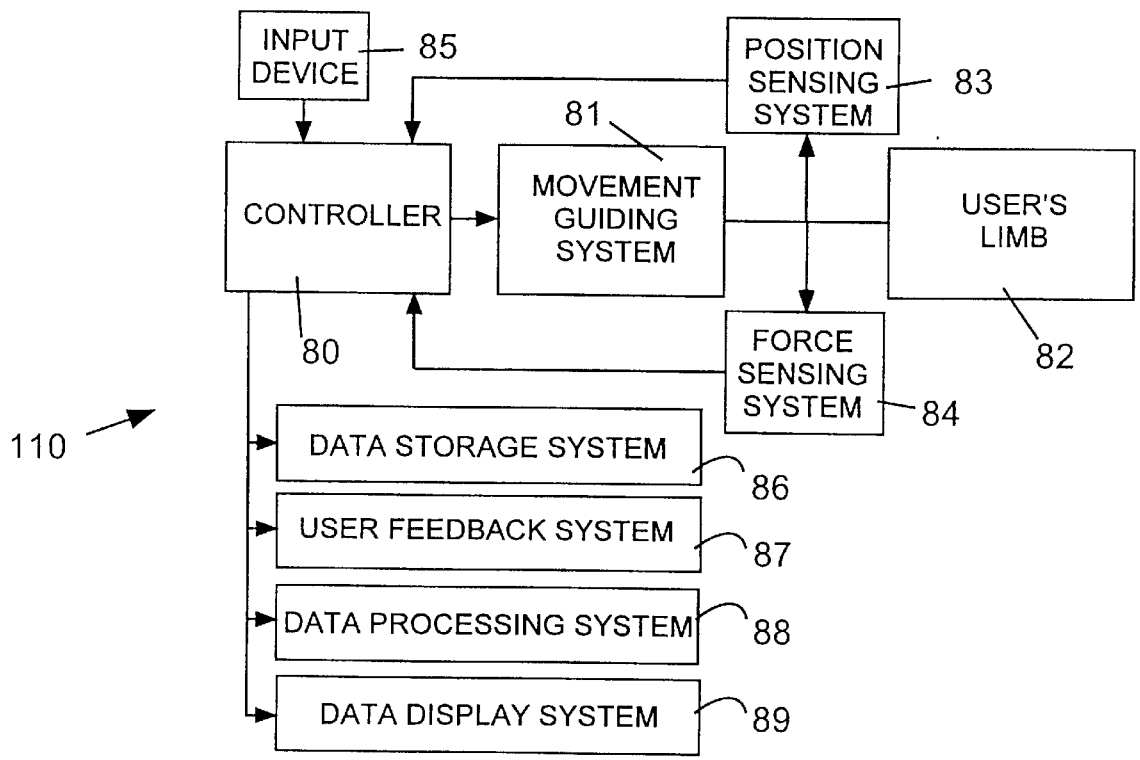
FIG. 5 is a block diagram of a preferred embodiment of the control system of the present invention.

As can be seen in FIG. 5, the control system 110 for guide 10 includes a controller 80 which receives commands from an input device 85. Controller 80 controls a movement guiding system 81 so that the movement guiding system 81 guides the movement of a user's limb 82. A position sensing system 83 measures the position of user's limb 82 along the movement guiding system 81. A force sensing system 84 measures the forces exerted by the user's limb 82 against the movement guiding system 81. Controller 80 receives position and force data from the position sensing system 83 and the force sensing system 84. It can also store data in a data storage system 86 and provide feedback to the user based on the data using a user feedback system 87. In addition, controller 80 can process the data using a data processing system 88 and can display data using a data display system 89.

Figure 6:
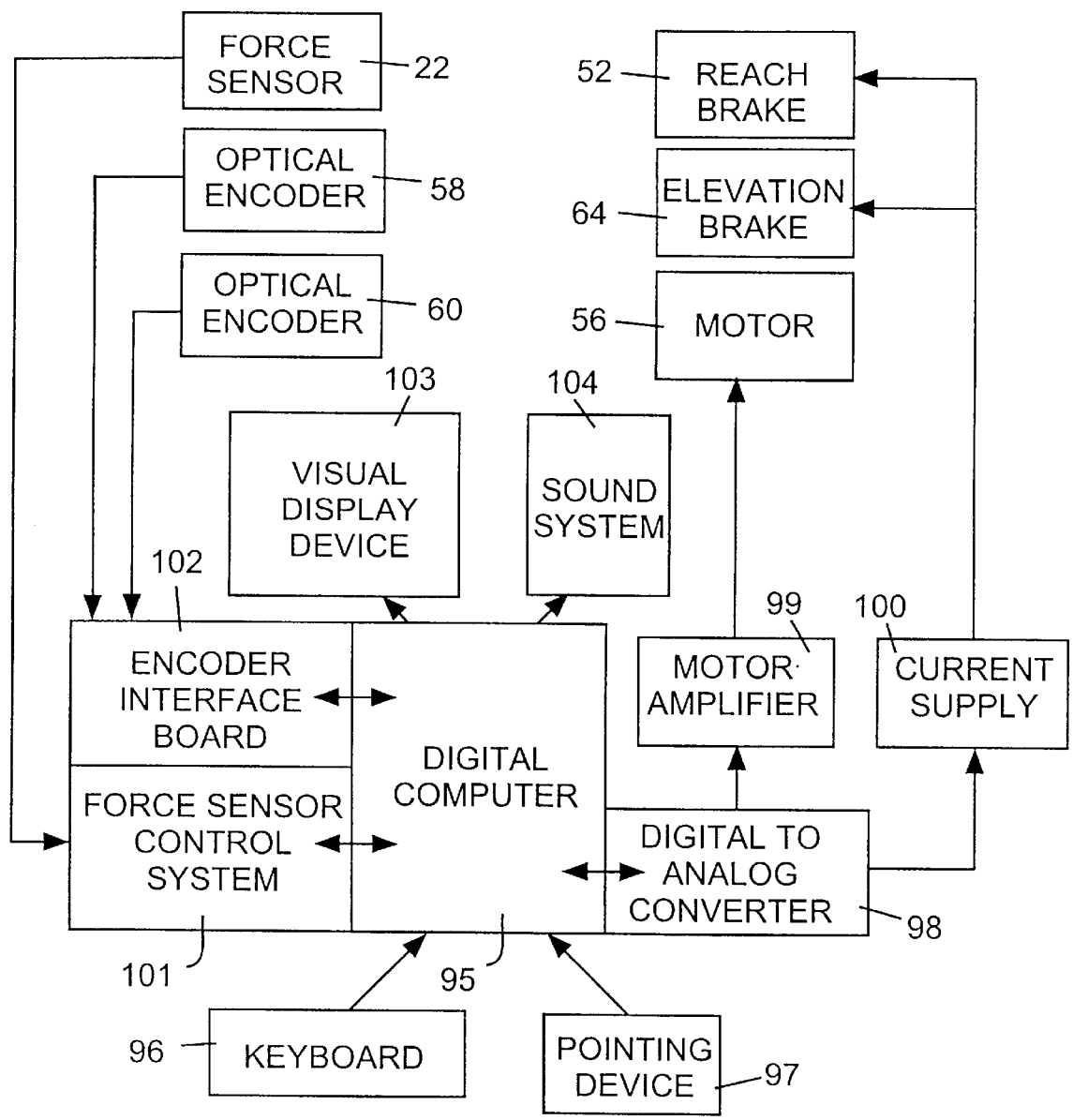
FIG. 6 is a block diagram of the sensing and control hardware used to implement the control system of the present invention.

FIG. 6 is a block diagram of the sensing and control hardware used in the preferred embodiment of the present invention to implement the control system of FIG. 5. The sensing hardware reads data from the force sensor 22, the optical encoder 58, and the optical encoder 60. The control hardware controls the reach brake 52, the elevation brake 64, and the motor 56. A digital computer 95 serves to process data. A force sensor control system 101 reads force values measured by the force sensor 22 and sends them to the digital computer 95. An encoder interface board 102 samples position values from optical encoders 58 and 60 and sends the values to digital computer 95. A visual display device 103 and a sound system 104 can provide feedback to the user about the movement performance and aid in the operation of measuring, storing, and displaying information from guide 10. Digital computer 95 can send commands to a current supply 100 and to a motor amplifier 99 through digital to analog converter 98 in order to control the resistance applied by brakes 52 and 64 and the force generated by the motor 56. A keyboard 96 and a pointing device 97 can be used to send instructions to the digital computer 95. In a preferred embodiment of the present invention, the digital computer is a Pentium-based 90 MHz PC clone available from Gateway 2000 Incorporated, Micron Electronics Incorporated or Dell Computer Corporation.

Figure 7:
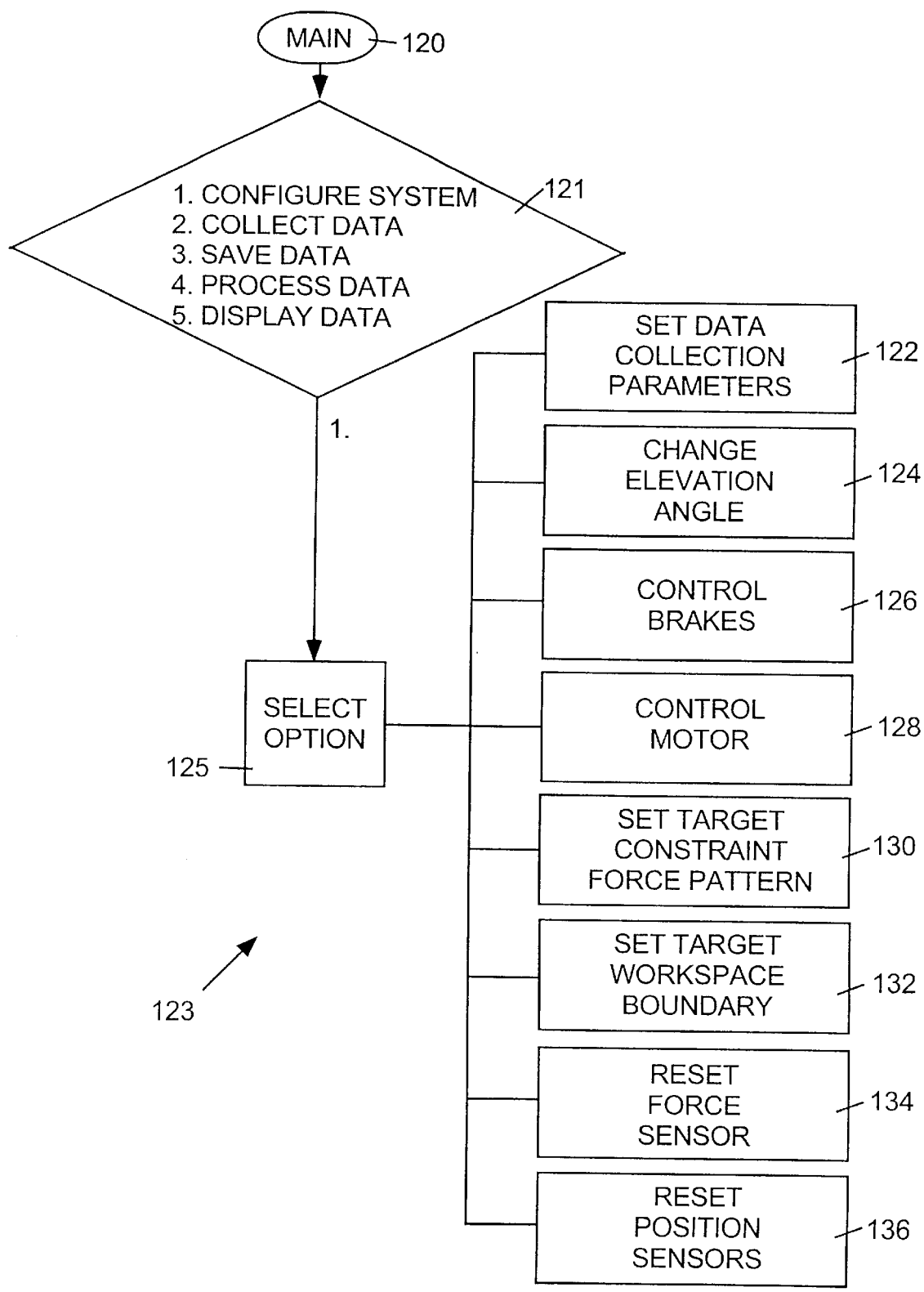
FIGS. 7–11 are flow charts illustrating routines which are utilized in the control system process of the present invention.

FIGS. 7–11 are flow charts illustrating routines which are utilized in the control system process of the present invention. Referring to FIG. 7, the control system process 123 is used to configure the operation of guide 10 by selecting the CONFIGURE SYSTEM option. Subroutine 122 can be selected to set data collection parameters such as the sampling rate, the duration of time for which to collect data, and the number of data collection channels to save. Subroutine 124 can be used to change the elevation angle of guide 10. In subroutine 124, a desired elevation angle is entered, the elevation brake 64 is released until guide 10 is moved to the desired elevation angle, and then the elevation brake 64 is set by control system 110. Subroutine 126 can be selected to change the resistance applied by brakes 52 and 64. Subroutine 128 can be used to change the control law applied by control system 110 to motor 56. Subroutine 130 can be used to specify a target constraint force pattern to be displayed on the visual display device 103. Subroutine 132 can be selected to specify a target workspace boundary to be displayed on the visual display device 103. Subroutines 134 and 136 can be used to reset the force and position sensors, respectively.

Figure 8:
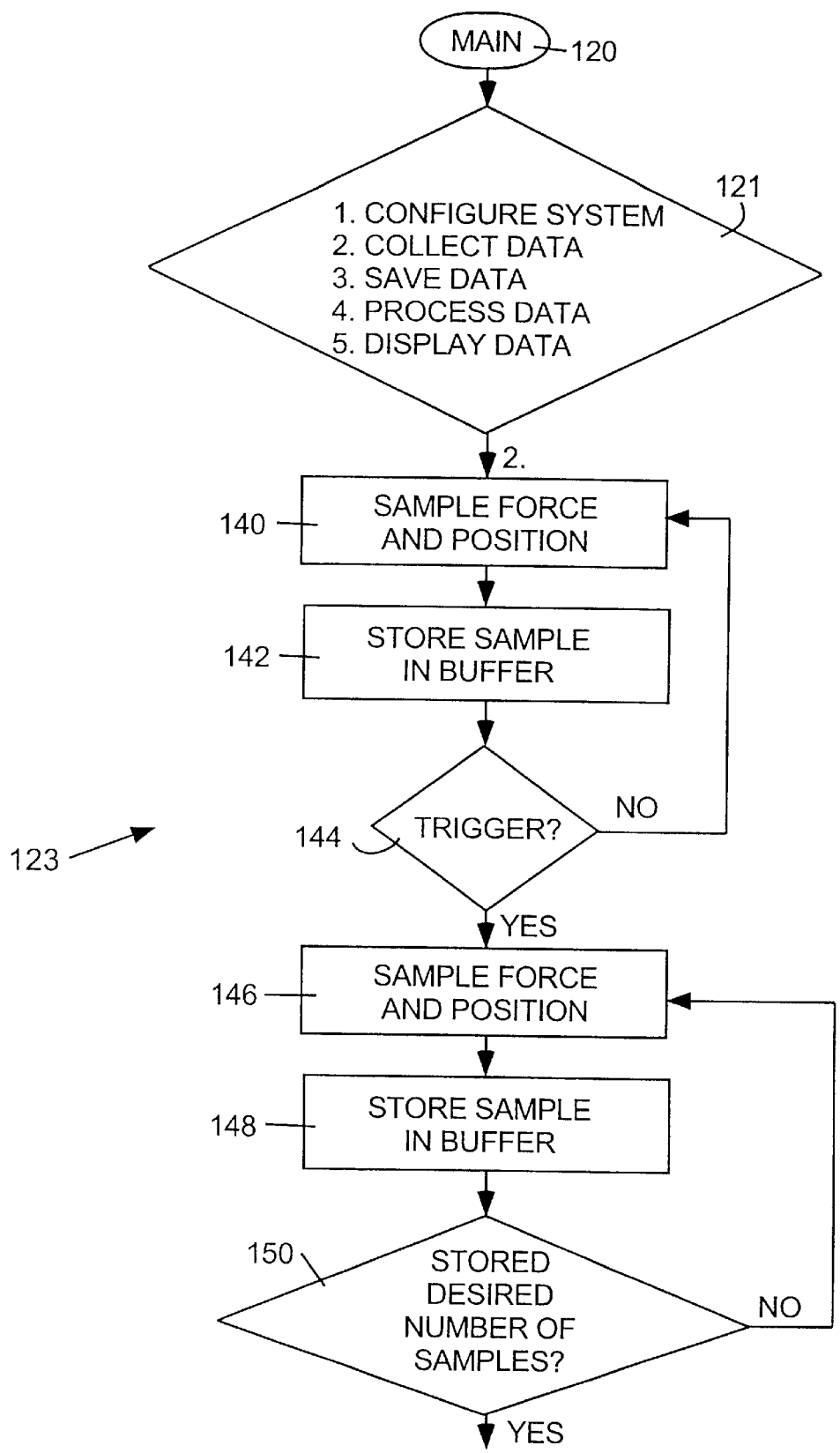

Referring to the flow chart of FIG. 8, the control system process 123 can initiate force and position data collection during the use of guide 10. Upon selection of the COLLECT DATA option, subroutine 140 causes the control system 110 to sample force and position data from position sensing system 83 and force sensing system 84. Data samples are stored in a circular buffer in the volatile memory of digital computer 95. Once the circular buffer is filled, the data is stored in the beginning of the buffer again. After a sample has been stored, subroutine 144 checks whether a trigger variable has been set. Different trigger functions are possible. For example, the trigger variable may be set if movement of the arm is initiated out of a specified window of position values. If the trigger is not set, force and position data are sampled again at the chosen sampling rate. If the trigger is set, force and position data are sampled again and stored in the circular buffer until the desired number of samples have been stored. Such a collection of samples is referred to as a "movement trial."

Figure 9:
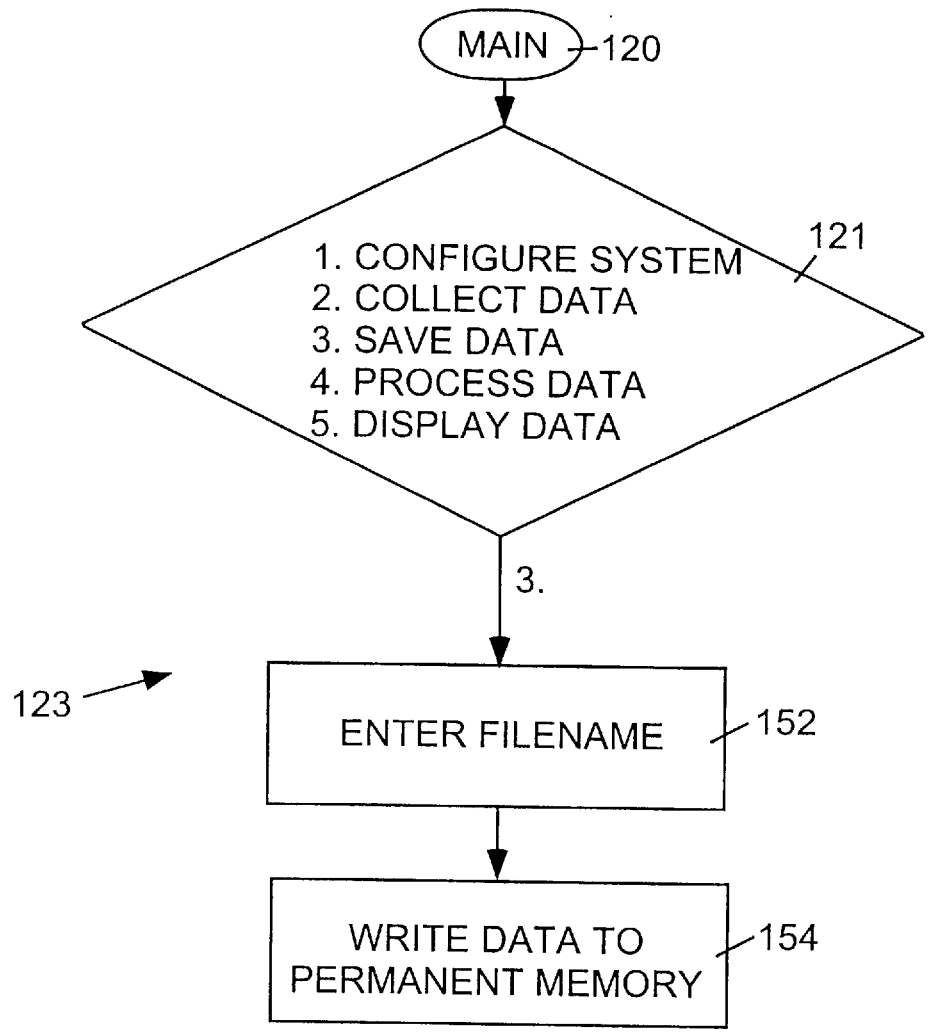

Referring to FIG. 9, the control system process 123 can control the saving of data to a permanent memory device. Upon selection of the SAVE DATA option, subroutine 152 prompts the user for a file name under which to save data stored in the volatile memory of digital computer 95. Subroutine 154 then writes the data to the permanent memory device.

Figure 10:
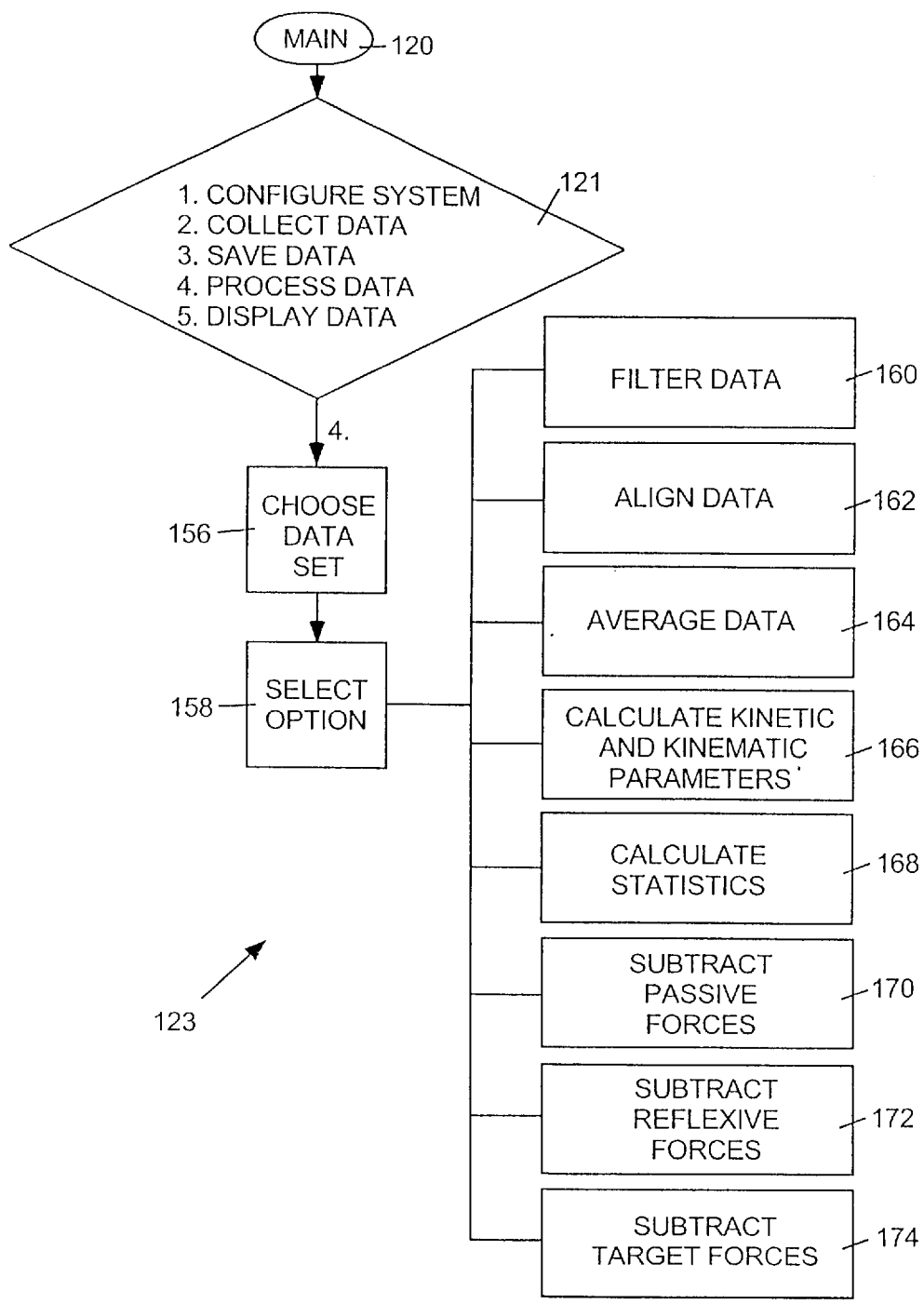

Referring to FIG. 10, the control system process 123 can control processing of data acquired from guide 10. Upon selection of the PROCESS DATA option, subroutine 156 prompts the user to choose which data set to process. A data set consists of one or more movement trials. Subroutine 158 then prompts the user to choose the desired data processing subroutine. Subroutine 160 can be selected to filter the data set. For example, a low pass filter, differentiating filter, or moving average filter can be applied to the data. Subroutine 162 can be selected to align all movement trials in the data set at some common temporal feature. For example, the movement trials can be aligned so that the first sample in each trial is the sample at which movement along the guide exceeded some threshold of velocity. Subroutine 164 can be selected to ensemble all average movement trials in the selected data set. Subroutine 166 can be selected to calculate kinetic and kinematic parameters of the movement trials such as the peak movement velocity, the extrema of movement, the constraint force at the time of peak movement velocity, the work done during the movement, or the torques exerted at the elbow and shoulder joints during the movement. Subroutine 168 can be selected to calculate statistics on data sets such as the standard deviation of the constraint forces, the average peak movement velocity in the data set, or the Student's t-test of the average constraint force of the currently selected data set as compared with the average constraint force of another data set. Subroutine 170 can be selected to subtract a measured set of passive forces from the forces of the movement trials in the data set. Similarly, subroutine 172 can be selected to subtract a measured set of reflexive forces from the forces of the movement trials in the data set. Subroutine 174 can be selected to subtract the desired target constraint forces from the actual constraint forces achieved by the subject during a movement attempt in order to calculate the target matching error. In some cases, subroutines 160–174 can be applied repeatedly in different orders to a data set. For example, it may be desirable to first filter a data set with subroutine 160, then align the filtered data with subroutine 162, then average the data with subroutine 164. Alternatively, it may be desirable to first calculate kinetic and kinematic parameters with subroutine 166, then calculate statistics on those parameters with subroutine 168.

Figure 11:
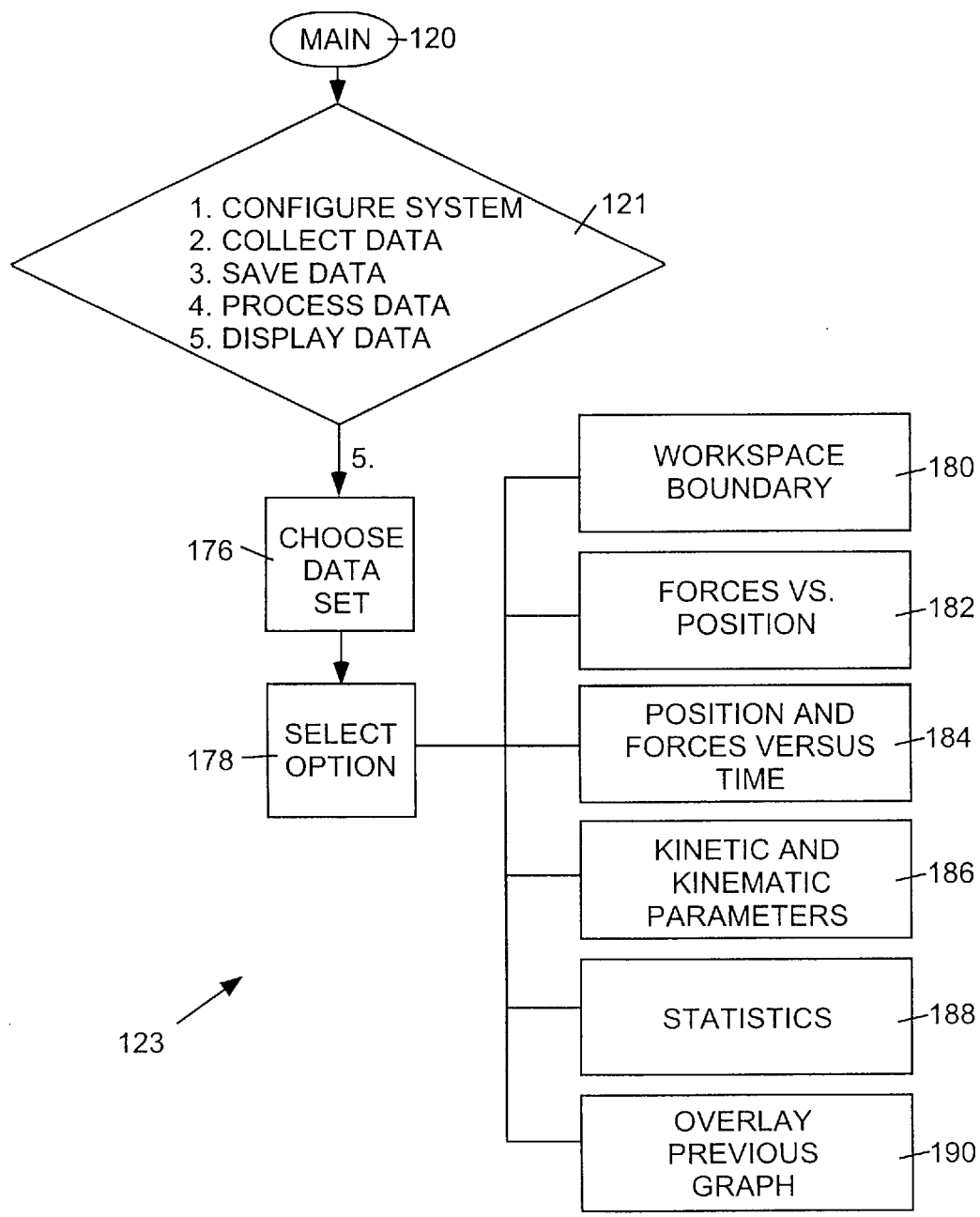

Referring to FIG. 11, the control system process 123 can control the display of data acquired from the guide. Upon selection of the DISPLAY DATA option, subroutine 176 prompts the user to choose which data set to display. Subroutine 178 then prompts the user to choose the desired data display subroutine. Subroutine 180 can be selected to display the workspace boundary consisting of the extrema of movement achieved along different guided movement paths. Subroutine 182 can be selected to display the constraint forces or tangent forces generated during a movement versus the position achieved along the guide. Subroutine 184 can be selected to display the forces generated and the position achieved during a movement versus the timing of the samples of the movement. Subroutine 186 can be selected to display various kinetic and kinematic parameters calculated with subroutine 166. Subroutine 188 can be selected to display statistics calculated with subroutine 168. Subroutine 190 can be selected to overlay a previously generated display with data from the currently chosen data set. For example, if subroutine 180 were selected to display the workspace boundary of a first data set, then a second data set could be specified using subroutine 176, and subroutine 190 could then be executed to overlay the workspace boundary of the second data set on the display of the first data set's workspace boundary.

Operation of the Preferred Embodiment

To use guide 10, the user's arm is connected to guide 10 via the user-attachment interface 14. Guide 10 is then configured to guide movement of the arm along a desired linear path. The position and orientation of the user 44 with respect to guide 10 can be adjusted by moving chair 46, adjusting the height of column 8, and setting guide 10 at a desired elevation angle using elevation brake 64.

In the preferred embodiment of the guide 10, to guide movement along a line, the elevation brake 64 is locked and movement occurs along splined shaft 2. Alternately, to guide movement along a circle, the reach brake 52 could be locked and movement could occur along a circle defined by the rotation of splined shaft 2 about axis B. In a further alternate embodiment, to guide movement along a vertical plane, both reach brake 52 and elevation brake 64 could be set to allow movement.

After the user 44 is attached to guide 10, the desired movement path is specified by adjusting guide 10 and chair 46. If the distance or orientation of the chair is changed with respect to the guide, the user's arm must necessarily follow a different path. For example, if the chair is rotated 45 degrees to the left with respect to the guide, the user's arm will travel along a path 45 degrees to the right side of the person's body. Thus, the orientation and position of the chair contribute to the orientation and location of the path followed by the arm. Once the desired path is specified, the guide 10 can be used in several different modes.

Figure 12:
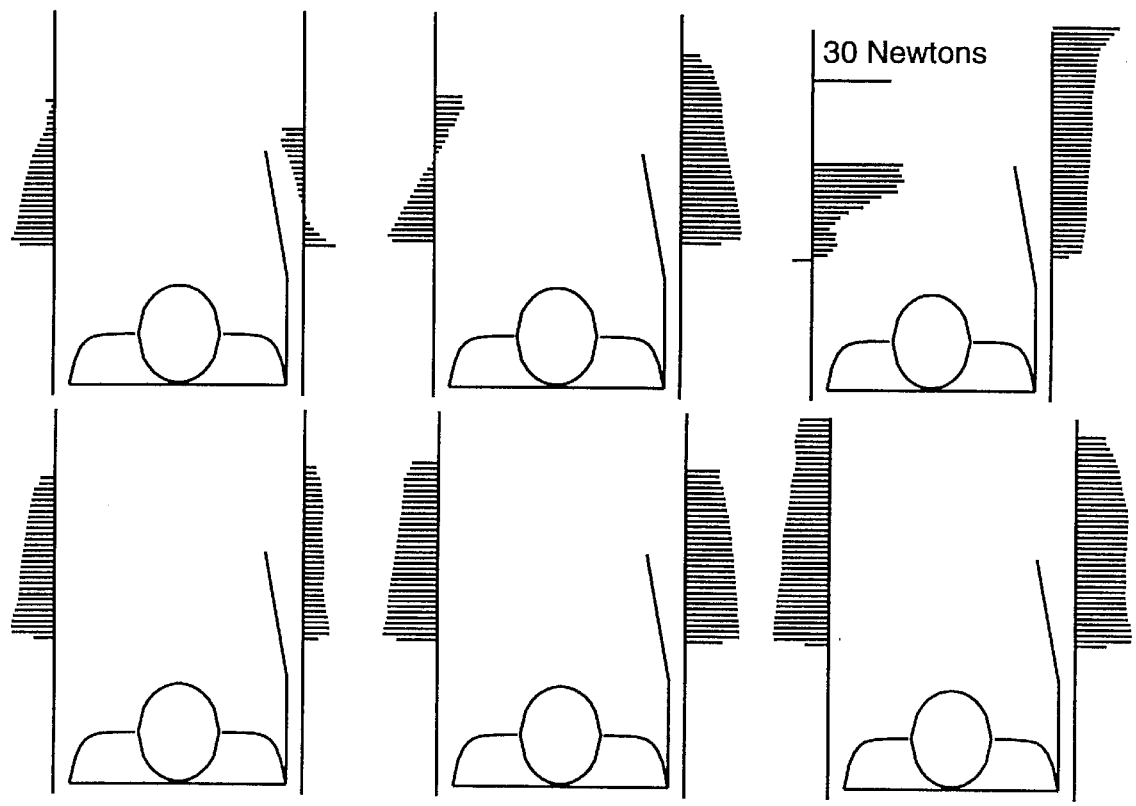
FIG. 12 illustrates the display of constraint force measurements generated by the present invention.

To quantify impaired movement performance along the specified path, user 44 attempts to move along guide 10. The constraint forces generated against guide 10 and the arm position along guide 10 are measured and stored by the control system process 123. As shown in FIG. 12, the control system process 123 can generate graphical representations of the constraint forces as a function of movement position. The lower set of representations show constraint forces generated by unimpaired users. The upper set of representations show constraint forces for hemiplegic users. Reach brake 52 and motor 56 can be used to provide resisting or assisting forces to the movement of the arm along the specified path. In an alternate embodiment of the present invention, the reach brake 52 and the motor 56 are used to impose constant velocity movement at a desired velocity on the user's arm. This is achieved by configuring the control system process 123 to provide feedback control of the reach velocity using reach brake 52 and motor 56. Any number of standard feedback control processes can be used.

To diagnose the relative contribution of different motor impairments to movement performance along a specified path, the following steps are followed. First, the constraint forces generated during voluntary movement of the impaired arm along the specified path are measured while reach brake 52 and motor 56 provide force so that the movement along guide 10 occurs at a constant specified velocity. To determine to what extent passive properties of the arm, including involuntary tonic muscle activity and changed connective tissue stiffness, contribute to the measured voluntary constraint force generation, the user 44 is instructed to attempt to relax the arm muscles. The user's arm is then passively moved along guide 10 at a slow enough rate to avoid exciting stretch reflexes. The arm can be passively moved by another person who grasps counterbalance 34 and moves the user's arm along the desired path. Alternately, motor 56 can be used to drive the arm along the desired path. Again, reach brake 52 and motor 56 provide force so that the arm moves at a constant velocity to eliminate inertial force generation by the arm.

As the user's arm is passively moved, the constraint forces generated against guide 10 and the movement position along guide 10 are measured and stored. The control system process 123 can be used to generate graphical representations of the passive constraint forces as a function of arm position. The control system process 123 can also calculate the difference between the passive and active constraint forces to diagnose how much of the voluntary constraint force generation is due to passive properties of the arm. In addition, to assess the degree to which the passive properties of an impaired arm are abnormal, the control system process 123 can compare the passive constraint forces generated by the impaired arm with the passive constraint forces generated by an unimpaired arm. The unimpaired arm can be the user's contralateral arm if user 44 is hemiplegic, or a similar sized arm in an unimpaired subject.

To diagnose the contribution of hyperactive stretch reflexes to impaired movement performance, the user 44 is instructed to attempt to relax all muscles in the arm and the user's arm is stretched at the same constant velocity as the previously measured voluntarily movement. The measured constraint forces are the sum of passive and reflexive constraint forces. Thus, to identify the contribution of reflexes to the measured constraint forces, the passive constraint forces must be subtracted from the measured constraint forces. The passive constraint forces can be identified as explained above by guiding the arm at a slow enough rate to avoid exciting stretch reflexes. Once the passive constraint forces are so identified, the control system can be used to subtract them from the measured constraint forces. The difference equals the constraint forces due to reflexes.

Figure 14A:
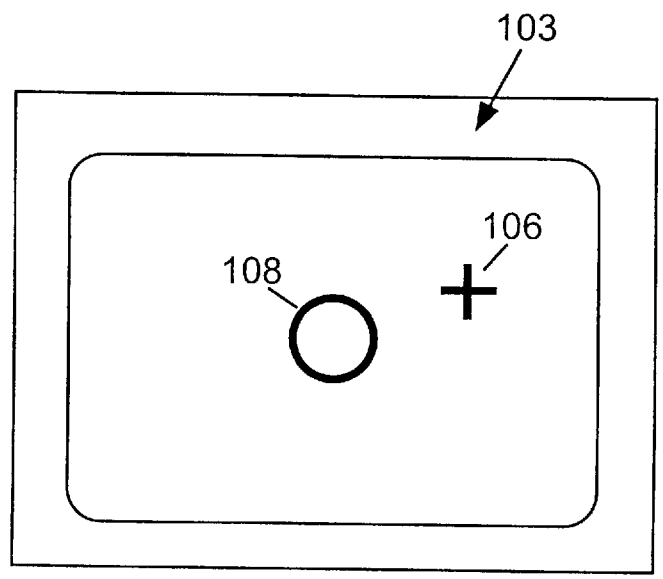
FIGS. 14a and 14b show different feedback displays of the present invention for helping the user improve movement performance.

Guide 10 can help user 44 in attempting to improve movement coordination by providing feedback about the size and direction of the constraint forces during movement attempts in a desired path. Referring to FIG. 14a, feedback can be given in the form of a graphical display on video display device 103. Cursor 106 represents the current constraint force value while circle 108 represents a desired target range for the constraint force. User 44 can then attempt to keep cursor 106 in the target range 108 during movement of the arm along guide 10. The control system process 123 can monitor and quantify the user's success at maturing the desired constraint force. For example, the distance between the current constraint force and the target constraint force can be averaged by data processing system 88 over the course of a movement to produce a measure of the overall target matching performance.

Figure 13:
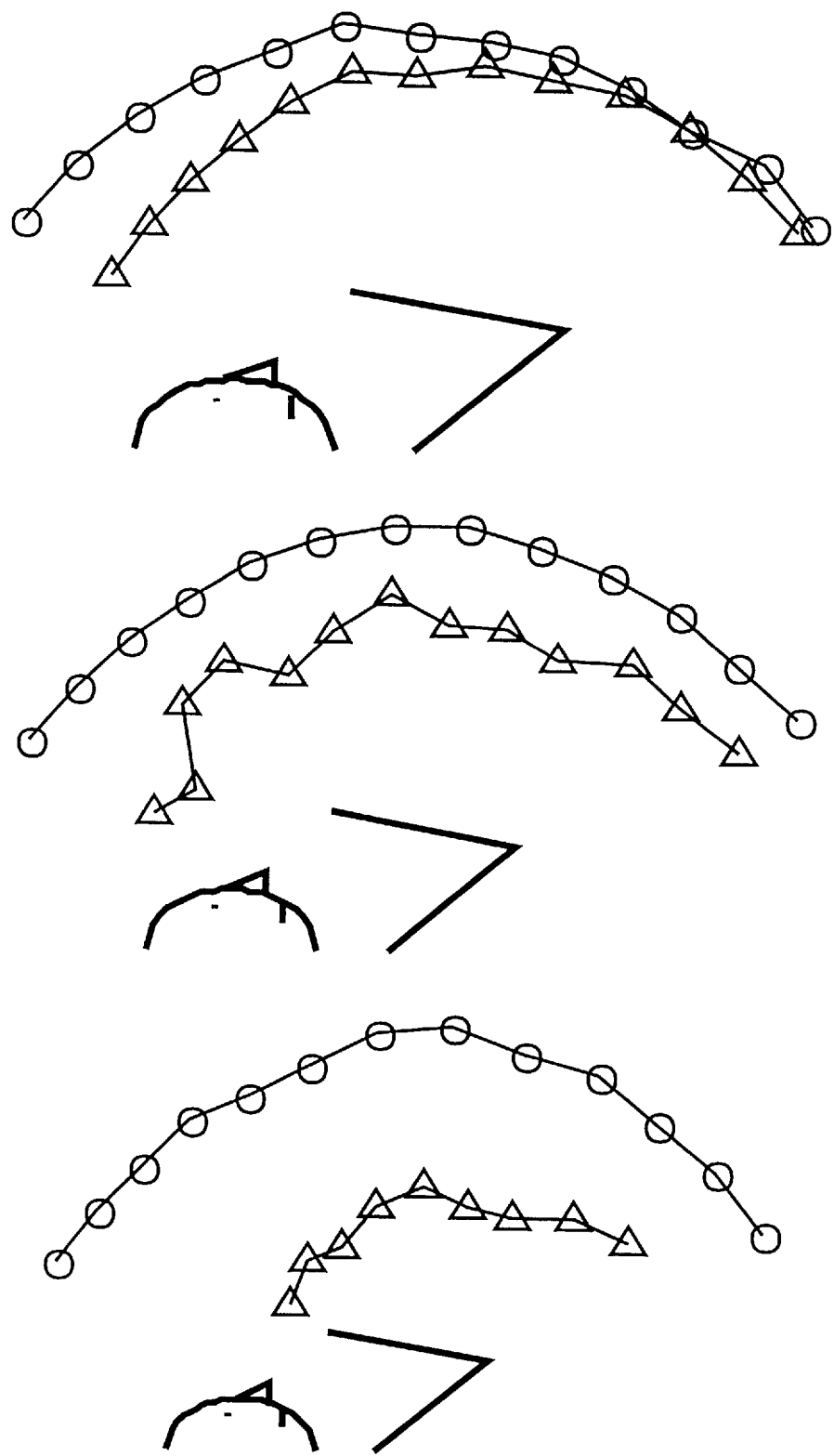
FIG. 13 illustrates the display of workspace measurements generated by the present invention.

Guide 10 can be used to identify regions of the arm's workspace into which user 44 has difficulty moving the arm. This is accomplished by orienting guide 10 so that movement is directed into the workspace region to be tested and then measuring the extrema of movement possible along guide 10 in that workspace region. Referring to FIG. 13, a graphical representation of the workspace boundary can be generated by the control system process 123 by varying the elevation angle of guide 10 and displaying the extrema of movement achieved by user 10 at different elevation angles. FIG. 13 includes graphical representations for three hemiplegic users. The movement achieved by the user's impaired arm at a certain angle can be compared to the movement that could be achieved by an unimpaired arm at the same angle. In FIG. 13, the boundaries marked with circles represent unimpaired arms while the boundaries marked with triangles represent impaired arms.

Guide 10 can be used to diagnose the cause of workspace deficits by comparing the extent of movement achieved during active movement to the extent of movement achieved during passive movement. For the passive movement, the user 44 attempts to relax the arm muscles as much as possible. Another person then grasps counterbalance 34 and moves the arm until the arm resists movement with a predetermined threshold of force. Alternately, motor 56 can be used to drive the arm slowly along the desired path. The control system process 123 can monitor the force of resistance in the desired direction of movement and indicate with a beep played on sound system 104 when the force of resistance exceeds a safe threshold. Alternately, the control system process 123 can terminate movement of motor 56 at the safe threshold of force of resistance. The position of the arm at the safe threshold defines the passive limit of movement of the arm in the guided direction. If the passive limit of movement is the same as the active limit, this indicates that passive arm properties, such as involuntary tonic muscle activity and changed connective tissue stiffness, limit the workspace.

Guide 10 can be used to diagnose the degree of impaired force generation at the workspace boundary by measuring the constraint force generated by the arm at the workspace boundary. If large constraint forces are generated at the workspace boundary as compared with an unimpaired arm, this indicates that the impaired arm cannot generate force in the desired direction at the boundary.

Guide 10 can be used to measure the resistance to movement of an impaired arm at the workspace boundary in the following way. User 44 moves the arm to its limit of movement along guide 10. If motion stops short of the normal full range of motion of the arm, motor 56 is used to move the arm farther along guide 10 by a predetermined amount such as, for example, two centimeters. The forces generated by the arm resisting the additional movement in the desired direction are recorded by the control system process 123. The resisting forces can be compared with the resisting forces generated by an unimpaired arm that is maximally activated against a resisting load in the same configuration as the impaired arm.

Figure 14B:
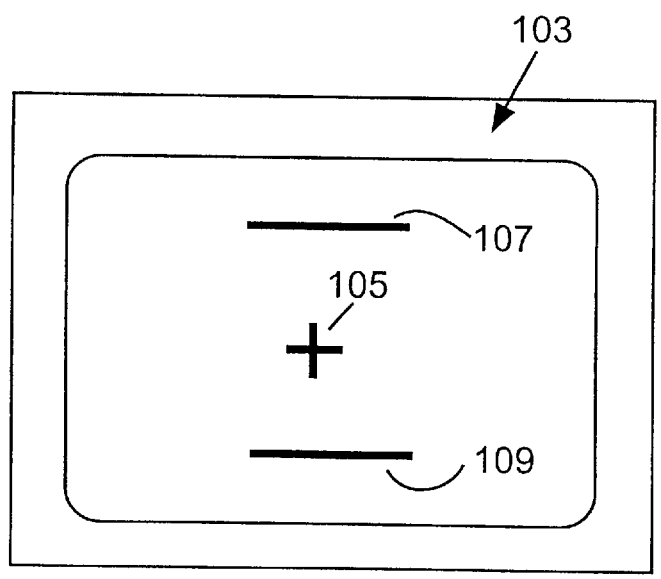

Guide 10 can help the user 44 attempt to improve movement performance by guiding movement attempts into difficult workspace regions. Referring to FIG. 14b, the control system process 123 can provide motivating feedback to the user about the extent of movement into those regions on visual display device 103. A cursor 105 shows the current extent of movement along guide 10 and bars 107 and 109 show the desired extent of motion. The user can attempt to move cursor 105 beyond either bar 107 or bar 109.

In view of the above, the guide 10 can be used to quantify impaired movement performance of a limb, to diagnose whether passive, active, or reflexive impairments limit movement performance, to quantify the resistance to movement provided by the limb at the workspace boundary, and to provide a means for a user to practice improving movement performance of the limb.

As mentioned above, the guide can be used with either arm of the user 44. Because the height of the guide can be vertically adjusted, the user could be sitting lying, or standing. Guide 10 may be used to quantify, diagnose, and treat impaired movement performance of the arms or legs of the user.

While the invention has been particularly shown and described with references to preferred embodiments thereof, it will be understood by those skilled in the art that various changes and form and details may be made therein without departing from the spirit and scope of the invention as defined by the dependent claims. For example, in an alternate embodiment, only one component of constraint force could be measured. In yet another alternate embodiment, movement could be guided along a circular or curved path, or a planar or curved surface, instead of along a linear path.

What is claimed:

1. A method for quantifying the movement impairment of a limb of a user using constraint forces, the method comprising the steps of:
 (a) guiding the movement of a limb along a path;
 (b) measuring the extent of movement of the limb along the path;
 (c) measuring the constraint forces applied by the limb; and
 (d) generating physical representations of the constraint forces applied as a function of the movement position of the limb along the path.

2. The method of claim 1 further comprising the step of:
 treating the movement impairment of the limb by providing feedback to the user of the constraint forces applied as a function of the movement position of the limb.

3. A method for diagnosing the movement impairment of a limb of a user using constraint forces, the method comprising the steps of:
 (a) measuring the constraint forces applied by a limb along a path during a constant velocity voluntary movement of the limb at a specified velocity;
 (b) measuring the constraint forces applied by the limb along the path during a slow, isovelocity imposed movement of the limb with the user attempting to relax all muscles of the limb, the slow imposed movement being at such a speed so as to avoid excitation of velocity-dependent reflexes in stretched muscles of the limb;
 (c) measuring the constraint forces applied by the limb along the path during an isovelocity voluntary movement of the limb at the specified speed with the user attempting to relax all muscles of the limb; and
 (d) comparing the constraint forces generated in steps (a)–(c).

4. A method for quantifying workspace deficits of a limb of a user, the method comprising the steps of:
 (a) guiding a limb along a path;
 (b) measuring the extrema of movement of the limb along the path;
 (c) varying the orientation of the path with respect to the user to allow for movement of the limb in different directions; and
 (d) generating a physical representation of the extrema of movement of the limb as a function of the orientation of the path, thereby identifying any workspace deficits of the limb.

5. The method of claim 4 further comprising the step of:
 treating the workspace deficits by providing feedback to the user about the extrema of movement as a function of the orientation of the path.

6. A method for diagnosing workspace deficits of a limb of a user, the method comprising the steps of:
 (a) guiding a limb along a path;
 (b) measuring the workspace boundary during passive imposed movements of the limb;
 (c) measuring the workspace boundary during voluntary movement of the limb; and
 (d) comparing the boundaries measured in steps (b) and (c) to determine whether passive properties of the limb limit the voluntary movement workspace of the limb.

7. The method of claim 6 further comprising the step of:
 measuring resistance to movement at the workspace boundary by moving the limb beyond the voluntary workspace boundary.

8. An apparatus for quantifying, diagnosing and treating movement impairment of a limb of a user using constraint forces comprising:
 means for guiding movement of a limb along a path;
 means for measuring the extent of movement of the limb along the path;
 means for measuring the constraint forces applied against the guiding means; and
 means for generating physical representations of the constraint forces as a function of movement position of the limb.

9. The apparatus of claim 8 wherein the guiding means further comprises a linear guiding means.

10. The apparatus of claim 9 wherein the means for measuring the constraint forces further comprises a force sensor sensing at least one component of force and operatively coupled to the guiding means so that it measures the constraint forces applied to the guiding means by the limb.

11. The apparatus of claim 8 further comprising means for providing feedback to the user of the constraint forces as a function of movement position of the limb.

12. The apparatus of claim 11 wherein the feedback providing means further comprises means for displaying the physical representations of the constraint forces to the user so that the user can attempt to improve control over the constraint forces.

13. The apparatus of claim 8 further comprising
 means for applying a controlled force to the limb, resulting in movement of the limb along the guiding means.

14. An apparatus for quantifying, diagnosing, and treating workspace deficits of a limb of a user comprising:
 means for guiding the movement of a limb along a path;
 means for measuring the extrema of movement of the limb along the path;
 means for varying the orientation of the guiding means with respect to the user to allow for the movement of the limb in different directions; and
 means for generating a physical representation of the extrema movement as a function of the guiding means orientation.

15. The apparatus of claim 14 wherein the guiding means further comprises a linear guiding means.

16. The apparatus of claim 15 wherein the measuring means further comprises a position sensor operatively connected to said guiding means for measuring the position of the limb along said guiding means.

17. The apparatus of claim 14 further comprising means for providing feedback to the user about the extrema of movement along the path.

18. The apparatus of claim 14 further comprising means for applying a controlled force to the limb, resulting in movement of the limb along the guiding means.

19. A movement guiding apparatus for quantifying, diagnosing, and treating impaired movement performance of a limb of a user, the apparatus comprising:
 means for coupling a limb of a user to the apparatus;
 means for guiding the limb along a path;
 means for varying the orientation of the guiding means with respect to the user to allow for the movement of the limb in different directions;
 means for measuring the movement of the limb along the path, means for measuring constraint forces and torque generated by the limb;
 control means for receiving the measured values in order to quantify, diagnose and treat the impaired movement performance of limbs;

means for generating a physical representation of constraint forces as a function of the movement of the limb; and means for generating a physical representation of the extent of movement as a function of the guiding means orientation.

20. The movement guiding apparatus of claim 19 wherein the coupling means comprises:

a cone handle which the user grasps; and a forearm brace connected to the cone handle for accommodating the user's forearm, the forearm brace being provided with a forearm strap for attaching the user's forearm to the brace.

21. The movement guiding apparatus of claim 20 wherein the coupling means further comprises a rotary shaft coupling the forearm brace to a shaft holding means, thereby enabling the coupling means to rotate in a plane parallel to the plane of the guiding means.

22. The movement guiding apparatus of claim 21 wherein the shaft holding means is operatively connected to the guiding means.

23. The movement guiding apparatus of claim 19 wherein the means for guiding the limb along a path comprises a linear guiding means.

24. The movement guiding apparatus of claim 23 wherein the linear guiding means further comprises:

a spline nut which is coupled to the coupling means; and a first splined shaft which is operatively coupled to the splined nut, the coupling means being guided along the shaft due to the interaction between the spline nut and the splined shaft.

25. The movement guiding apparatus of claim 24 wherein the linear guiding means further comprises:

a chain which extends along the length of the first splined shaft and is operatively coupled to the coupling means; and a first sprocket provided at a distal end of the first splined shaft and operatively coupled to the chain, the coupling means being guided along the length of the first splined shaft by the cooperation of the coupling means with the splined shaft and the chain.

26. The movement guiding apparatus of claim 25 wherein the linear guiding means further comprises:

a second splined shaft provided adjacent to the first splined shaft; and a counterbalance operatively connected to the second splined shaft and the chain.

27. The movement guiding apparatus of claim 26 wherein the linear guiding means further comprises a member being connected to a proximal end of the first and second shafts; and a second sprocket provided adjacent to the member, the second sprocket being operatively coupled to the chain.

28. The movement guiding apparatus of claim 19 further comprising a drive box operatively coupled to the guiding means via a drive shaft, the drive shaft extending through the drive box.

29. The movement guiding apparatus of claim 28 wherein the drive box houses:

first braking means for holding the guiding means at different elevation angles, the first braking means comprises a portion of the means for varying the orientation of the guiding means;

second braking means for applying braking torque to the drive shaft; and motor means for applying torque to the drive shaft.

30. The movement guiding apparatus of claim 29 further including a hollow shaft which extends about the drive shaft, is operatively connected to the first braking means, and comprises a portion of the means for varying the orientation of the guiding means.

31. The movement guiding apparatus of claim 30 wherein the drive box further houses:

a first position sensor associated with the first braking means for measuring the rotation of the hollow shaft; and a second position sensor associated with the second braking means for measuring the rotation of the drive shaft.

32. The movement guiding apparatus of claim 29 wherein each braking means comprises a magnetic particle brake.

33. The movement guiding apparatus of claim 29 wherein the motor means comprises a direct current torque motor.

34. The movement guiding apparatus of claim 19 wherein the means for measuring constraint forces and torque further comprises a force sensing means operatively coupled to the coupling means whereby, when the coupling means is guided along a path, the force sensing means measures the force and torque generated by the user's limb against the coupling means.

35. The movement guiding apparatus of claim 34 wherein the force sensing means measures three orthogonal components of force and three orthogonal components of torque.

36. The movement guiding apparatus of claim 19 wherein the control means further comprises means for quantifying impaired movement of the limb.

37. The movement guiding apparatus of claim 19 wherein the control means further comprises means for quantifying workspace deficits of the limb.

38. The movement guiding apparatus of claim 19 wherein the control means further comprises means for diagnosing impaired movement of the limb.

39. The movement guiding apparatus of claim 19 wherein the control means further comprises means for diagnosing workspace deficits of the limb.

40. The movement guiding apparatus of claim 19 wherein the control means further comprises means for treating impaired movement of the limb.

41. The movement guiding apparatus of claim 19 wherein the control means further comprises means for treating workspace deficits of the limb.

* * * * *